(12) United States Patent
Yao et al.

(10) Patent No.: US 11,377,647 B2
(45) Date of Patent: Jul. 5, 2022

(54) AMYLASE MUTANT HAVING HIGH SPECIFIC ACTIVITY AND THERMAL STABILITY, GENE OF MUTANT, AND APPLICATIONS THEREOF

(71) Applicant: INSTITUTE OF ANIMAL SCIENCE OF CHINESE ACADEMY OF AGRICULTURAL SCIENCES, Beijing (CN)

(72) Inventors: Bin Yao, Beijing (CN); Huiying Luo, Beijing (CN); Jin Qiu, Beijing (CN); Tao Tu, Beijing (CN); Huoqing Huang, Beijing (CN); Yuan Wang, Beijing (CN); Yaru Wang, Beijing (CN); Yingguo Bai, Beijing (CN); XiaoYun Su, Beijing (CN); Kun Meng, Beijing (CN)

(73) Assignee: INSTITUTE OF ANIMAL SCIENCE OF CHINESE ACADEMY, Beijing (CN)

( * ) Notice: Subject to any disclaimer, the term of this patent is extended or adjusted under 35 U.S.C. 154(b) by 0 days.

(21) Appl. No.: 16/982,628

(22) PCT Filed: Mar. 21, 2019

(86) PCT No.: PCT/CN2019/079000
§ 371 (c)(1),
(2) Date: Sep. 21, 2020

(87) PCT Pub. No.: WO2019/179485
PCT Pub. Date: Sep. 26, 2019

(65) Prior Publication Data
US 2021/0024908 A1    Jan. 28, 2021

(30) Foreign Application Priority Data
Mar. 21, 2018 (CN) .......................... 201810235559.0

(51) Int. Cl.
*C12N 9/28* (2006.01)
*C12N 1/20* (2006.01)
*C12N 15/75* (2006.01)

(52) U.S. Cl.
CPC ........... *C12N 9/2417* (2013.01); *C12N 15/75* (2013.01); *C12Y 302/01001* (2013.01)

(58) Field of Classification Search
CPC .................................................... C12N 9/2417
See application file for complete search history.

(56) References Cited

FOREIGN PATENT DOCUMENTS

WO    WO-2013184577 A1  * 12/2013 ..... C12Y 302/01001

OTHER PUBLICATIONS

Studer. Residue mutations and their impact on protein structure and function: detecting beneficial and pathogenic changes. Biochem. J. (2013) 449, 581-594.*

* cited by examiner

*Primary Examiner* — Yong D Pak
(74) *Attorney, Agent, or Firm* — Patshegen IP LLC; Moshe Pinchas

(57) ABSTRACT

The present invention relates to the field of agriculture biotechnology, specially relates to an amylase mutant having high specific activity and thermal stability, gene and use thereof. Said amylase mutant is obtained by performing substitution of S33A/S34E/V35H, and deletion of amino acids at the sites of 178 and 179 of the wild type amylase having amino acid sequence of SEQ ID NO:1, and having improved enzymatic activity and thermal stability than the wild type amylase.

7 Claims, 2 Drawing Sheets
Specification includes a Sequence Listing.

SEQUENCE LISTING

<160> NUMBER OF SEQ ID NOS: 6

<210> SEQ ID NO 1
<211> LENGTH: 485
<212> TYPE: PRT
<213> ORGANISM: Bacillus amyloliquefaciens

<400> SEQUENCE: 1

```
Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365
```

```
Tyr Gly Thr Lys Gly Thr Thr Thr Arg Glu Ile Pro Ala Leu Lys Ser
    370             375                 380
Lys Ile Glu Pro Leu Leu Lys Ala Arg Lys Asp Tyr Ala Tyr Gly Thr
385                 390                 395                 400
Gln Arg Asp Tyr Ile Asp Asn Pro Asp Val Ile Gly Trp Thr Arg Glu
                405                 410                 415
Gly Asp Ser Thr Lys Ala Lys Ser Gly Leu Ala Thr Val Ile Thr Asp
            420                 425                 430
Gly Pro Gly Gly Ser Lys Arg Met Tyr Val Gly Thr Ser Asn Ala Gly
            435                 440                 445
Glu Ile Trp Tyr Asp Leu Thr Gly Asn Arg Thr Asp Lys Ile Thr Ile
450                 455                 460
Gly Ser Asp Gly Tyr Ala Thr Phe Pro Val Asn Gly Ser Val Ser
465                 470                 475                 480
Val Trp Val Gln Gln
                485

<210> SEQ ID NO 2
<211> LENGTH: 483
<212> TYPE: PRT
<213> ORGANISM: Artificial Sequence
<220> FEATURE:
<223> OTHER INFORMATION: synthesized mutant

<400> SEQUENCE: 2

Ala Ala Thr Asn Gly Thr Met Met Gln Tyr Phe Glu Trp Tyr Val Pro
1               5                   10                  15
Asn Asp Gly Gln Gln Trp Asn Arg Leu Arg Thr Asp Ala Pro Tyr Leu
                20                  25                  30
Ala Glu His Gly Ile Thr Ala Val Trp Thr Pro Pro Ala Tyr Lys Gly
            35                  40                  45
Thr Ser Gln Ala Asp Val Gly Tyr Gly Pro Tyr Asp Leu Tyr Asp Leu
        50                  55                  60
Gly Glu Phe Asn Gln Lys Gly Thr Val Arg Thr Lys Tyr Gly Thr Lys
65                  70                  75                  80
Gly Glu Leu Lys Ser Ala Val Asn Thr Leu His Ser Asn Gly Ile Gln
                85                  90                  95
Val Tyr Gly Asp Val Val Met Asn His Lys Ala Gly Ala Asp Tyr Thr
                100                 105                 110
Glu Asn Val Thr Ala Val Glu Val Asn Pro Ser Asn Arg Asn Gln Glu
            115                 120                 125
Thr Ser Gly Glu Tyr Asn Ile Gln Ala Trp Thr Gly Phe Asn Phe Pro
        130                 135                 140
Gly Arg Gly Thr Thr Tyr Ser Asn Phe Lys Trp Gln Trp Phe His Phe
145                 150                 155                 160
Asp Gly Thr Asp Trp Asp Gln Ser Arg Ser Leu Ser Arg Ile Phe Lys
                165                 170                 175
Phe Thr Gly Lys Ala Trp Asp Trp Glu Val Ser Ser Glu Asn Gly Asn
                180                 185                 190
Tyr Asp Tyr Leu Met Tyr Ala Asp Ile Asp Tyr Asp His Pro Asp Val
            195                 200                 205
Val Asn Glu Met Lys Lys Trp Gly Val Trp Tyr Ala Asn Glu Val Gly
        210                 215                 220
Leu Asp Gly Tyr Arg Leu Asp Ala Val Lys His Ile Lys Phe Ser Phe
225                 230                 235                 240
```

```
Leu Lys Asp Trp Val Asp Asn Ala Arg Ala Ala Thr Gly Lys Glu Met
                245                 250                 255

Phe Thr Val Gly Glu Tyr Trp Gln Asn Asp Leu Gly Ala Leu Asn Asn
            260                 265                 270

Tyr Leu Ala Lys Val Asn Tyr Asn Gln Ser Leu Phe Asp Ala Pro Leu
        275                 280                 285

His Tyr Asn Phe Tyr Ala Ala Ser Thr Gly Gly Tyr Tyr Asp Met
    290                 295                 300

Arg Asn Ile Leu Asn Asn Thr Leu Val Ala Ser Asn Pro Thr Lys Ala
305                 310                 315                 320

Val Thr Leu Val Glu Asn His Asp Thr Gln Pro Gly Gln Ser Leu Glu
                325                 330                 335

Ser Thr Val Gln Pro Trp Phe Lys Pro Leu Ala Tyr Ala Phe Ile Leu
            340                 345                 350

Thr Arg Ser Gly Gly Tyr Pro Ser Val Phe Tyr Gly Asp Met Tyr Gly
        355                 360                 365

Thr Lys Gly Thr Thr Thr Arg Glu Ile Pro Ala Leu Lys Ser Lys Ile
    370                 375                 380

Glu Pro Leu Leu Lys Ala Arg Lys Asp Tyr Ala Tyr Gly Thr Gln Arg
385                 390                 395                 400

Asp Tyr Ile Asp Asn Pro Asp Val Ile Gly Trp Thr Arg Glu Gly Asp
                405                 410                 415

Ser Thr Lys Ala Lys Ser Gly Leu Ala Thr Val Ile Thr Asp Gly Pro
            420                 425                 430

Gly Gly Ser Lys Arg Met Tyr Val Gly Thr Ser Asn Ala Gly Glu Ile
        435                 440                 445

Trp Tyr Asp Leu Thr Gly Asn Arg Thr Asp Lys Ile Thr Ile Gly Ser
    450                 455                 460

Asp Gly Tyr Ala Thr Phe Pro Val Asn Gly Gly Ser Val Ser Val Trp
465                 470                 475                 480

Val Gln Gln

<210> SEQ ID NO 3
<211> LENGTH: 50
<212> TYPE: DNA
<213> ORGANISM: Artificial Sequence
<220> FEATURE:
<223> OTHER INFORMATION: synthesized primer

<400> SEQUENCE: 3
ttacaaaaac atcagccgta ggatccgccg caacgaacgg aacaatgatg           50

<210> SEQ ID NO 4
<211> LENGTH: 54
<212> TYPE: DNA
<213> ORGANISM: Artificial Sequence
<220> FEATURE:
<223> OTHER INFORMATION: synthesized primer

<400> SEQUENCE: 4
gggacgtcga cttagtggtg gtggtggtgg tgctgctgaa cccacactga gacg       54

<210> SEQ ID NO 5
<211> LENGTH: 51
<212> TYPE: DNA
<213> ORGANISM: Artificial Sequence
<220> FEATURE:
<223> OTHER INFORMATION: synthesized primer
```

```
<400> SEQUENCE: 5
gggttcagca gcaccaccac caccaccact aagtcgacgt ccccggggca g         51

<210> SEQ ID NO 6
<211> LENGTH: 50
<212> TYPE: DNA
<213> ORGANISM: Artificial Sequence
<220> FEATURE:
<223> OTHER INFORMATION: synthesized primer

<400> SEQUENCE: 6
attgttccgt tcgttgcggc ggatcctacg gctgatgttt ttgtaatcgg            50
```

AMYLASE MUTANT HAVING HIGH SPECIFIC ACTIVITY AND THERMAL STABILITY, GENE OF MUTANT, AND APPLICATIONS THEREOF

FIELD OF THE INVENTION

The present invention relates to the field of genetic engineering, particularly to an amylase mutant having high specific activity and thermal stability, gene and application thereof.

BACKGROUND OF THE INVENTION

Amylase, also known as 1,4-α-D-glucan hydrolase (EC 3.2.1.1), is an enzyme that can hydrolyze α-1,4-glycosidic bond in starch, which has been widely applied to food, medicine, feed, textile and other industries.

At present, the industrially produced amylase is mainly from *Bacillus*. The conventional methods of producing the amylase focus on obtaining high-yield strains with UV or the chemical mutagens, and optimizing the fermentation conditions of the strains to further improve the enzyme production capacity of strains. However, the fermentation process of *Bacillus* is relatively complex, and has the drawbacks of low yield and uneven fermentation products, which is disadvantageous to the later processing technology. Therefore, the genetic engineering technology is applied to improve amylase production. Although the heterologous expression of amylase is realized by genetic engineering technology, it's still to resolve the problem of the high production cost caused by the low expression level, which limits the large-scale industrial production and application of the amylase. Therefore, the method of the protein engineering is applied to molecular modification of the amylase to improve its catalytic performance.

Order of the Invention

One order of the present invention is to provide a amylase mutant obtained by mutation of site or sites of the amino acid sequence of the amylase from *Bacillus amyloliquefaciens*.

Another order of the present invention is to provide a gene encoding the above mutant.

Another order of the present invention is to provide a recombinant vector comprising the gene encoding the above mutant.

Another order of the present invention is to provide a recombinant cell comprising the gene encoding the above mutant.

SUMMARY OF THE INVENTION

In one aspect, the present invention provides an amylase mutant which is obtained by performing substitution of S33A/S34E/V35H to acid amino sequence of the wild type amylase with amino acid sequence as shown in SEQ ID No:1, and removing amino acids of the sites of 178 and 179, or an amylase mutant having 90-99% sequence identity to the amylase obtained by performing the substitution of S33A/S34E/V35H to the acid amino sequence of the wild type amylase with amino acid sequence as shown in SEQ ID No:1, and removing amino acids of the sites of 178 and 179, wherein said amylase mutant has 2.5-3.5 times activity of the wild type amylase, remains more than 99% of its initial activity after 5 min's incubation at 70° C., and remains 32% of its initial activity after 5 min's incubation at 80° C.

SEQ ID No: 1:
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFRGTGKAWDWEVSSENGNYDYLMY

ADIDYDHPDVVNEMKKWGVWYANEVGLDGYRLDAVKHIKFSFLKDWVDNA

RAATGKEMFTVGEYWQNDLGALNNYLAKVNYNQSLFDAPLHYNFYAASTG

GGYYDMRNILNNTLVASNPTKAVTLVENHDTQPGQSLESTVQPWFKPLAY

AFILTRSGGYPSVFYGDMYGTKGTTTREIPALKSKIEPLLKARKDYAYGT

QRDYIDNPDVIGWTREGDSTKAKSGLATVITDGPGGSKRMYVGTSNAGEI

WYDLTGNRTDKITIGSDGYATFPVNGGSVSVWVQQ*

In a preferred embodiment the amylase mutant according to the present invention has the amino sequence of SEQ ID NO: 2.

SEQ ID NO: 2:
AATNGTMMQYFEWYVPNDGQQWNRLRTDAPYLAEHGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWEVSSENGNYDYLMYAD

IDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ*

In a yet preferred embodiment of the present invention, said amylase mutant is the mutant obtained substitution, deletion and/or insertion of one or more, e.g., 1, 2, 3, 4, 5, 6, 7, 8 or 9, amino acid residues of polypeptide of SEQ ID NO:2, and maintaining the properties of the above amylase mutant. For example, a common strategy is substitutions of the conservative amino acid that the amino acid residue is replaced with another amino acid residue having a similar side chain without effect on the properties of the enzyme. Families of amino acid residues having similar side chains have been defined in the art. Furthermore, it is well known in the art that the suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions of the proteins, in order to construct a fusion protein, to enhance expression of recombinant protein, to obtain an recombinant protein automatically secreted outside the host cell, or to aid in the purification of the recombinant protein.

In a further preferred embodiment, a mutant amylase has the sequence identity of least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more to the full amino acid sequence of SEQ ID NO:2. Ranges and identity values intermediated to the above-recited values are also intended to be included in the present invention.

According to the prior art in the art, the mutant refers to the individual which is obtained by mutation of the wild type protein, and has the phenotypic characteristics different from the wild type. A person skilled in the art can obtain the mutant having the new properties by replacing, inserting or deleting specific nucleotides of the DNA sequence under the condition of knowing the structure and function of the protein.

In a further preferred embodiment the present invention provides the gene encoding the above amylase mutant having high activity and thermostability. The said gene can be the molecule of DNA, cDNA, mRNA, hnRNA, or tRNA.

In a further preferred embodiment, the present invention provides a gene having a nucleotide sequence which hybridizes to a nucleotide sequence of SEQ ID NO: 2 under stringent conditions. As used here, the term "hybridize under stringent conditions" refers to the hybridization and cleaning conditions in which at least 90% of homologous nucleotide sequences can still be hybridized with each other. The said stringent condition are well known to those skilled in the art and can be found in current protocols in molecular biology, John Wiley & Sons, N.Y. (1989), 6.3.1-6.3.6. One example of hybridization under stringent conditions is hybridization in 6×SSC at 45° C., then washing one or more times at 50-65° C. in 0.2×SSc and 0.1% SDS. Those skilled in the art can understand that highly stringent conditions can be achieved by increasing the hybridization temperature, for example, to 50° C., 55° C., 60° C. or 65° C.

In addition, those skilled in the art will understand that there may exist the genetic polymorphism due to natural variation among individuals of a population. The gene encoding the amylase mutant of the present invention may have such natural variation without changing the activity of the mutant. Therefore, the present invention also includes alleles of a gene encoding a polypeptide having an amino acid sequence of SEQ ID No:2.

In another aspect, the present invention provides recombinant vector comprising the gene encoding the abovementioned amylase mutant. In a preferred embodiment of the present invention, the said recombinant vector is constructed based on the vector of pHYP16. The recombinant expression vectors of the invention can be designed for expressing amylase in prokaryotic or eukaryotic cells. For example, amylase can be expressed in bacterial cells such as *E. coli*, yeast such as *Pichia* or *Aspergillus*, insect cells such as Sf9 cell or silkworm cell with baculovirus expression vectors, or plant cell such as *Arabidopsis*, tobacco, corn, and so on, mediated by *Agrobacterium tumefaciens*. Thus, the invention relates to host cells introduced with a recombinant expression vector of the invention. The host cells of the present invention may be any prokaryotic or eukaryotic cell, including but not limited to the above host cells. Preferably, said host cell is *Pichia* preferred. *Pichia pastoris* is methylotrophic yeast, capable of metabolizing methanol as its sole carbon source. This system is well-known for its ability to express high levels of heterologous proteins. As an effective expression system, many of the gene encoding the amylase have successfully expressed in *P. pastoris*. The novel gene encoding the mutant amylase of the present invention is also expressed in *P. pastoris* with high levels. So it will be very easy to mass-produce the polygalacturonase by fermentation in the lower cost than ever.

In a preferred embodiment, the vector DNA can be transferred into prokaryotic or eukaryotic cells by the conventional transformation or transfection methods. Appropriate methods for transforming or transfecting host cells can be found in the second edition of *Molecular cloning* (Sambrook et al.), and other laboratory manuals.

In a preferred embodiment, the present invention provides a recombinant strain comprising the above gene encoding the said mutant amylase. Preferably, said recombinant strain is *E coli*, yeast such as *Pichiapastoris* cell, *Saccharomyces cerevisiae*, or *Hansenulapolymorpha, Bacillus* or *Lactobacillus*, more preferably *Bacillus* SCK6 cells.

In another aspect, the present invention also relates to a method of producing amylase having high activity and thermostability comprising the steps of:

(1) transforming a host cell with the DNA construct or a recombinant vector of comprising said gene encoding the above amylase mutant to obtain the recombinant host cell;

(2) cultivating the recombinant host cell to induce the expression of amylase; and (3) isolating and recovering said amylase Compared with the wild-type amylase, the mutant amylase of the present invention has the following profiles: (1) having the increased enzyme activity which is the 2.5-3.5 times of the wild type, such as 2.5 times, 2.6 times, 2.7 times, 2.8 times, 2.9 times, 3.0 times, 3.1 times, 3.2 times, 3.3 times, 3.4 times or 3.5 times; (2) having the improved thermostability of retaining more than 99% of activity for 3 to 10 min, such as 3 min, 4 min, 5 min, 6 min, 7 min, 9 min or 10 min, at 70° C., and retaining 30% to 35% of activity for 3 min, 4 min, 5 min, 6 min, 7 min, 9 min or 10 min at 80° C.

In another aspect, the invention provides the application of the amylase mutant with high specific activity and thermal stability, wherein said mutant amylase can be applied to food, medicine, animal feed and/or textile industry.

Also, the invention provides the application of gene encoding the above mutant amylase to food, medicine, animal feed and/or textile industry.

The present invention overcomes the shortcomings of the prior art and provides a amylase mutant with high enzyme activity and excellent thermal stability, which can be applied to food, medicine, feed, textile industry, etc. The mutant S33A/S34E/V35H/Δ R178/G179 of the present invention has the enzyme activity increasing to 17067.57 U/Mg from 5553.53 U/mg of wild type; still retains more than 99% of the enzyme activity after being treated at 70° C. for 5 min, compared with remaining 10% for the wild type; and retains 32% of the enzyme activity after being treated at 80° C. for 5 min, compared with almost losing all of enzyme activity for the wild type. Therefore, the amylase mutant amylase of the present invention can meet the requirements of application in food, medicine, feed and textile industry, and has a very broad application prospect.

BRIEF DESCRIPTIONS OF THE DRAWINGS

EMBODIMENT

Figure 1:
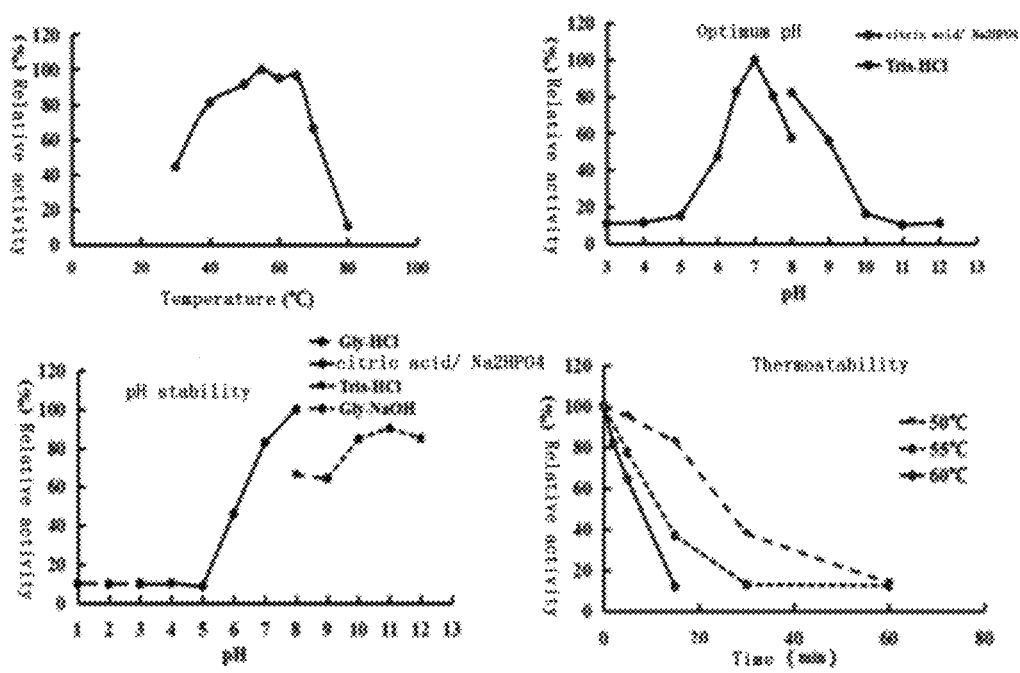
FIG. 1 shows the enzymatic properties of the wild-type amylase.

The present invention is further illustrated with reference to the following examples and the appended drawings, which should by no means be construed as limitations of the present invention.

Test Materials and Reagents

1. Strains and vectors: host: *Bacillus subtilis* SCK6; and vector pHYP16-BKAMY
2. Enzymes and other biochemical reagents: restriction endonucleases (Fermentas); and ligase (Promaga).
3. Medium: LB medium; starch medium Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Site Directed Mutagenesis of the Gene Encoding the Amylase

The optimized mutation site wasS33A/S34E/V35H/ ΔR178/Δ G179. The mutation site was introduced with the primers of table 1 by Site-directed Mutagenesis Kit followed by sequencing to obtain the mutant gene.

TABLE 1

| SEQ ID NO. | Primers | Sequence (5'→ 3')[a] | Length (bp) |
|---|---|---|---|
| 3 | Bkamy-F | ttacaaaaacatcagccgtaggatccg ccgcaacgaacggaacaatgatg | 50 |
| 4 | Bkamy-R | gggacgtcgacttagtggtggtggtgg tggtgctgctgaacccacactgagacg | 54 |
| 5 | pHYP16-F | gggttcagcagcaccaccaccaccacc actaagtcgacgtccccggggcag | 51 |
| 6 | pHYP16-R | attgttccgttcgttgcggcggatcct acggctgatgttttgtaatcgg | 50 |

Sequencing results showed that the nucleotide sequence amplified by mutation had 1458 bp, comprising the encoding area of 1455 bp encoding the amino acid sequence of SEQ ID No: 2 having 485 amino acid residues. The protein with the amino acid sequence of SEQ ID No: 2 was named as amylase mutant BKAMYA.

Example 2 Preparation of Amylase Mutant BKAMYA

1. Preparation of Recombinant Plasmid pHYP16-BKAYA

Firstly, the vector and the target fragment were amplified by POE-PCR followed by being recovered and mixed in a proper proportion, and then added into the PCR system to construct the recombinant plasmid containing the said amylase gene. Mutation of nucleotides was introduced by Site Mutation kit using the wild type plasmid as the temple. Then, the obtained recombinant plasmid was sequenced to test the validity of purpose sequence. The recombinant plasmid inserting the exogenous gene was named asp-HYP16-BKAMYA.

2. Preparation of the Recombinant Strain SCK6/BKA-MYA

The above recombinant plasmid pHYP16-BKAMYA was transformed into *Bacillus* spk6 cells to obtain the recombinant strain SCK6/BKAMYA.

3. Preparation of the Amylase Mutant

The above recombinant strainSCK6/BKAMYA was inoculated into 50 mL of medium in 100 mL of flask and cultured on a shaker operating at 220 rpm at 37° C. and for 24 h. Then, the cultured medium was transferred to 200 mL medium in a 1 L of flask to culture at 37° C. and 220 RPM again. The supernatant was collected by centrifugation to purify the amylase mutant BKAMYA by affinity chromatography for analyzing activity.

Example 3 Analysis and Comparison of the Amylase Mutant BKAMYA and Wild Type Amylase 1. Analysis and Comparison of the Enzymatic Activity The enzymatic activity of amylase was determined with UV spectrophotometer by the steps of performing the enzymatic reaction at the certain temperature and pH for 20 min, wherein 1 mL of said enzymatic reaction system included 100 μL of appropriate diluted enzyme solution and 900 μL of substrate, measuring the absorbance at 540 nm and calculating the enzymatic activity. A unit of enzymatic activity (U) is defined as the amount of enzyme to produce 1 μmol glucose per unit time under given conditions.

The purified amylase mutant prepared in example 2 and the wild type amylase were performing the enzymatic reaction at pH 7.0 and 55° C. to determine their enzymatic activity.

As showed in FIG. 1, the enzymatic activity of wild type is 5553.53 U/Mg, and that of amylase mutant is 17067.57 U/mg.

2. Analysis and Comparison of Thermal Stability

The thermal stability of both the purified amylase mutant prepared in example 2 and the wild type was determined by treating at 60° C. for 10 min, 30 min and 60 min respectively or 70° C. for 2 min, 5 min, and 10 min respectively, in 0.1 mol/L of citric acid-disodium hydrogen phosphate buffer (pH 7.0), and their retained enzymatic activity at 55° C. was determined.

Figure 2:
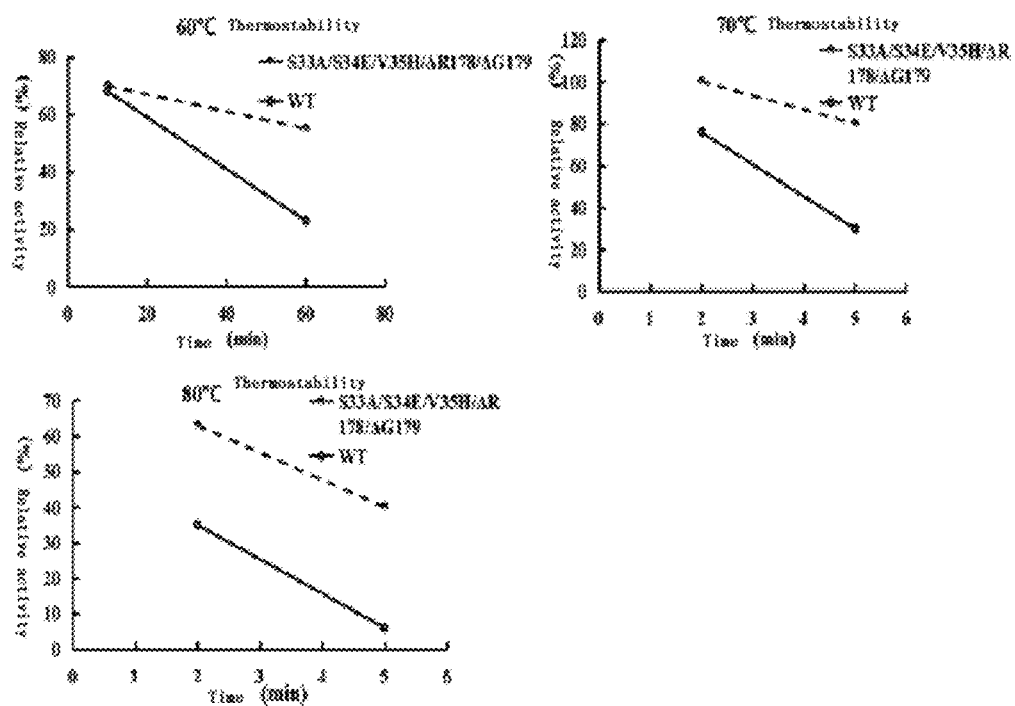
FIG. 2 shows the comparison of thermal stability of the amylase mutant with that of the wild-type amylase.
Figure 3:
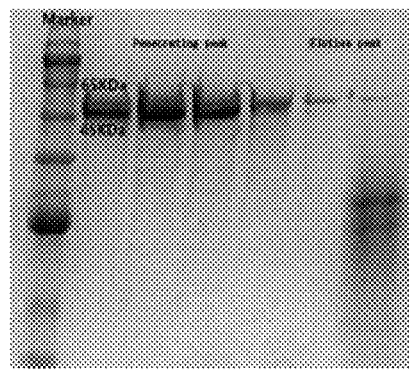
FIG. 3 shows the SDS-PAGE electrophoresis results of amylase expressed in *Bacillus subtilis* sck6.

As showed in FIG. 2, the mutant S33A/S34E/V35H/ ΔR178/G179 retained more than 99% of enzymatic activity, but the wild type amylase retained about 10% of enzymatic activity, after being treated at 70° C. for 5 min; and, the mutant retained 32% of enzymatic activity, but the wild type almost lost enzymatic activity after being treated at 80° C. for 5 min. And, the specific activity of mutant was increased to 17067.57 U/mg compared with that of the wild type amylase.

The invention claimed is:

1. An amylase mutant, having the amino acid sequence of SEQ ID NO: 2.

2. A gene comprising a nucleotide sequence encoding the amylase mutant of claim 1.

3. A recombinant vector of comprising the gene of claim 2.

4. An isolated recombinant cell comprising the gene of claim 2.

5. A method of preparing amylase having high enzymatic activity and thermal stability, comprising the steps of
   (1) constructing a recombinant vector comprising the gene of claim 2;
   (2) transforming an isolated host cell with the recombinant vector obtained by the step (1); and
   (3) cultivating the recombinant host cell and isolating said amylase.

6. A method of preparing a feed, medicine, or food, comprising incubating the amylase mutant of claim 1 with a feed, medicine, or food comprising an α-1,4-glycosidic bond, to hydrolyze said α-1,4-glycosidic bond.

7. A method of preparing a feed, medicine, or food, comprising incubating the gene of claim 2 with a feed, medicine, or food comprising an α-1,4-glycosidic bond, to hydrolyze said α-1,4-glycosidic bond.

* * * * *